US012779097B2

(12) United States Patent
Chen

(10) Patent No.: US 12,779,097 B2
(45) Date of Patent: Nov. 3, 2026

(54) ISOLATED WEARABLE BREAST PUMP

(71) Applicant: Shenzhen TPH Technology Co., Ltd., Shenzhen (CN)

(72) Inventor: Xianzi Chen, Shenzhen (CN)

(73) Assignee: Shenzhen TPH Technology Co., Ltd., Shenzhen (CN)

( * ) Notice: Subject to any disclaimer, the term of this patent is extended or adjusted under 35 U.S.C. 154(b) by 553 days.

(21) Appl. No.: 18/240,189

(22) Filed: Aug. 30, 2023

(65) Prior Publication Data

US 2024/0399035 A1 Dec. 5, 2024

(30) Foreign Application Priority Data

Jun. 5, 2023 (CN) ........................ 202321411576.8

(51) Int. Cl.
*A61M 1/06* (2006.01)

(52) U.S. Cl.
CPC .................................. *A61M 1/067* (2021.05)

(58) Field of Classification Search
CPC ........ A61M 1/064; A61M 1/06; A61M 1/062; A61M 1/067; A61M 1/73; A61M 1/732; A61M 1/734; A61M 1/78
See application file for complete search history.

(56) References Cited

U.S. PATENT DOCUMENTS

| | | | | | |
|---|---|---|---|---|---|
| 5,169,291 | A * | 12/1992 | Zebuhr | F24H 9/133 417/393 |
| 6,369,714 | B2 * | 4/2002 | Walter | D06F 39/081 340/618 |
| 10,480,824 | B2 * | 11/2019 | Gardner | F24H 15/12 |
| 10,508,422 | B2 * | 12/2019 | Sharratt | F16K 31/05 |
| 11,273,240 | B2 * | 3/2022 | Zhang | A61M 1/06 |
| 11,541,156 | B2 * | 1/2023 | Hwang | A61M 1/064 |
| 2003/0216119 | A1 * | 11/2003 | Mashiko | F21S 45/33 454/275 |
| 2020/0384172 | A1 * | 12/2020 | Kim | A61M 1/064 |
| 2021/0030934 | A1 * | 2/2021 | Zhang | A61M 1/06935 |
| 2021/0369927 | A1 * | 12/2021 | Hwang | A61M 1/06 |
| 2024/0001008 | A1 * | 1/2024 | Chen | A61M 1/06 |
| 2024/0001010 | A1 * | 1/2024 | Chen | A61M 1/066 |

* cited by examiner

*Primary Examiner* — Quynh-Nhu H. Vu

(57) ABSTRACT

The present disclosure discloses an isolated wearable breast pump comprising a milk collecting casing for storing milk, and a breast pump main unit connected to the milk collecting casing for drawing air inside the milk collecting casing, wherein the connection surface between the milk collecting casing and the breast pump main unit is provided with a ventilation structure, which is provided with a waterproof means used to prevent liquid from entering the breast pump main unit. Compared with the prior art, the present disclosure only has one ventilation structure connecting the breast pump main unit with the milk collecting casing, and a waterproof means is disposed on the ventilation structure, on the one hand, to reduce the risk of contamination arising from milk's contact with the breast pump main unit, and on the other hand, to avoid the breast pump main unit from damaging due to milk's penetration.

7 Claims, 5 Drawing Sheets

ISOLATED WEARABLE BREAST PUMP

CROSS-REFERENCE TO RELATED PATENT APPLICATION

This application claims priority to and the benefit of Chinese Patent Application No. CN202321411576.8 filed in China on Jun. 5, 2023. The disclosure of the above application is incorporated herein in its entirety by reference.

TECHNICAL FIELD

The present disclosure relates to the field of mother-and-baby-related products, in particular an isolated wearable breast pump.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Lactating women can use a breast pump in the hospital or at home to suck milk out of their breasts, and their congestive symptoms can ease after using the breast pump for lactation. At present, of the wearable breast pump on the market, the surface of the main unit housing is directly connected with the diaphragm part of the milk storage container to form a negative pressure cavity, and the diaphragm moves forwards and backwards under the cooperation of the vacuum pump and the solenoid valve to achieve sucking milk. Since the diaphragm is a deformable soft rubber material, it is prone to breakage, which makes it easy for milk to contact the breast pump main unit and enter the main unit, resulting in short circuit damage inside the breast pump main unit.

SUMMARY

In view of the problem that liquid is easy to enter the breast pump main unit and cause a short circuit in the prior art, the present disclosure provides an isolated wearable breast pump.

The technical solution of the disclosure is to provide an isolated wearable breast pump comprising a milk collecting casing for storing milk, and a breast pump main unit connected to the milk collecting casing for drawing air inside the milk collecting casing, wherein the connection surface between the milk collecting casing and the breast pump main unit is provided with a ventilation structure, which is provided with a waterproof device used to prevent liquid from entering the breast pump main unit.

Further, the ventilation structure includes a ventilation column disposed on the connection surface of the milk collecting casing and the breast pump main unit, and a ventilation hole disposed on the breast pump main unit and cooperating with the ventilation column.

Further, the ventilation hole adopts a soft rubber material, the ventilation column adopts a hard rubber material, and the ventilation column is closely plugged in and in sealing connection with the ventilation hole.

Further, the waterproof device comprises a waterproof membrane disposed on the ventilation hole and/or the ventilation column.

Further, a vacuum pump connected to the ventilation structure and used to draw the air in the milk collecting casing is arranged inside the breast pump main unit;

the waterproof device further includes a liquid sensor disposed at the ventilation structure and a waterproof valve connected to the liquid sensor, the vacuum pump and the ventilation structure intercommunicate with each other though the waterproof valve, which closes when the liquid sensor is triggered.

Further, at least one first suction member is disposed on the connection surface between the milk collecting casing and the breast pump main unit, and at least one second suction member is disposed at the position fitting with the breast pump main unit.

Further, there are two first suction members, and the ventilation structure is arranged close to the perpendicular bisector of the connection line of the two first suction members.

Further, the milk collecting casing further has a connecting portion for fitting with mammillae, and a negative pressure cavity connected to the connecting portion;

the breast pump main unit is connected to the negative pressure cavity and used to draw air in the negative pressure cavity.

Further, the connection surface between the milk collecting casing and the breast pump main unit is provided with a milk pouring port, which has an inclination towards the outside of the milk collecting casing.

Compared with the prior art, the present disclosure has at least the following beneficial effects:

Since the isolated wearable breast pump provided by the present disclosure only has one ventilation structure connecting the breast pump main unit with the milk collecting casing, it can completely eliminate the contact between the internal diaphragm inside the milk collecting casing and the breast pump main unit, even if the diaphragm is broken, it can reduce the contact between milk and the breast pump main unit. The present disclosure also provides a waterproof device on the ventilation structure, on the one hand, to reduce the risk of contamination arising from milk's contact with the breast pump main unit, and on the other hand, to avoid the breast pump main unit from damaging due to milk's penetration.

BRIEF DESCRIPTION OF THE DRAWINGS

In order to more clearly illustrate the technical solution in the examples of the present disclosure, we shall make a detailed description in combination with the drawings and examples as follows.

DETAILED DESCRIPTION OF SOME EMBODIMENTS

We shall describe in detail the principle and structure of the present disclosure in combination with the drawings and examples as follows.

The isolated wearable breast pump provided by the present disclosure includes the milk collecting casing 1 for storing milk, and the breast pump main unit 2 connected to the milk collecting casing 1 for drawing air inside the milk collecting casing 1, the connection surface 4 between the milk collecting casing 1 and the breast pump main unit 2 is provided with the ventilation structure 3, which is provided with a waterproof device used to prevent liquid from entering the breast pump main unit 2.

Figure 1:
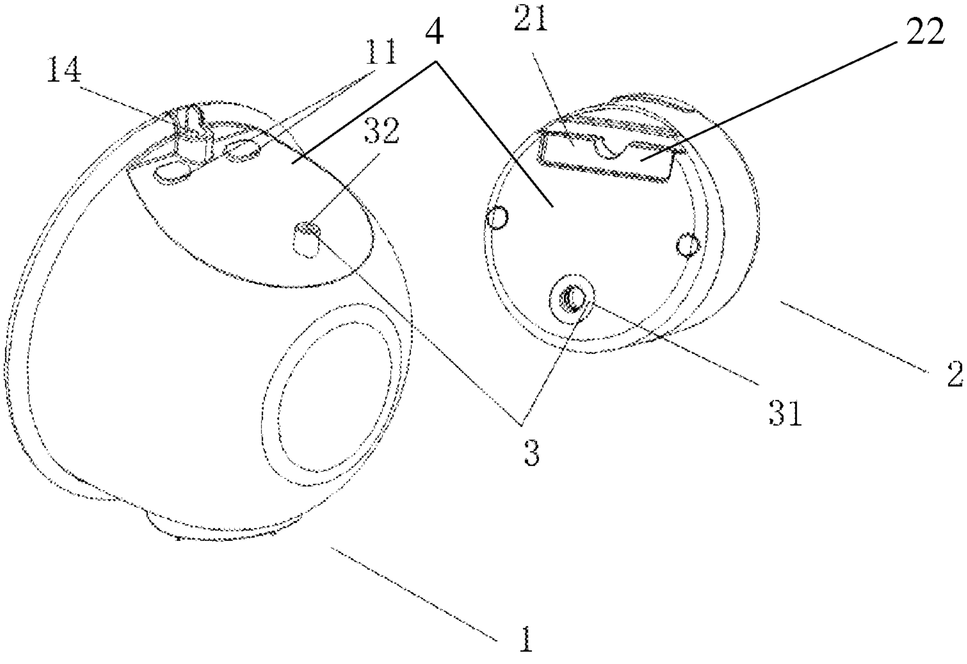
FIG. 1 is an exploded view of the breast pump main unit and the milk collecting casing according the present disclosure.
Figure 2:
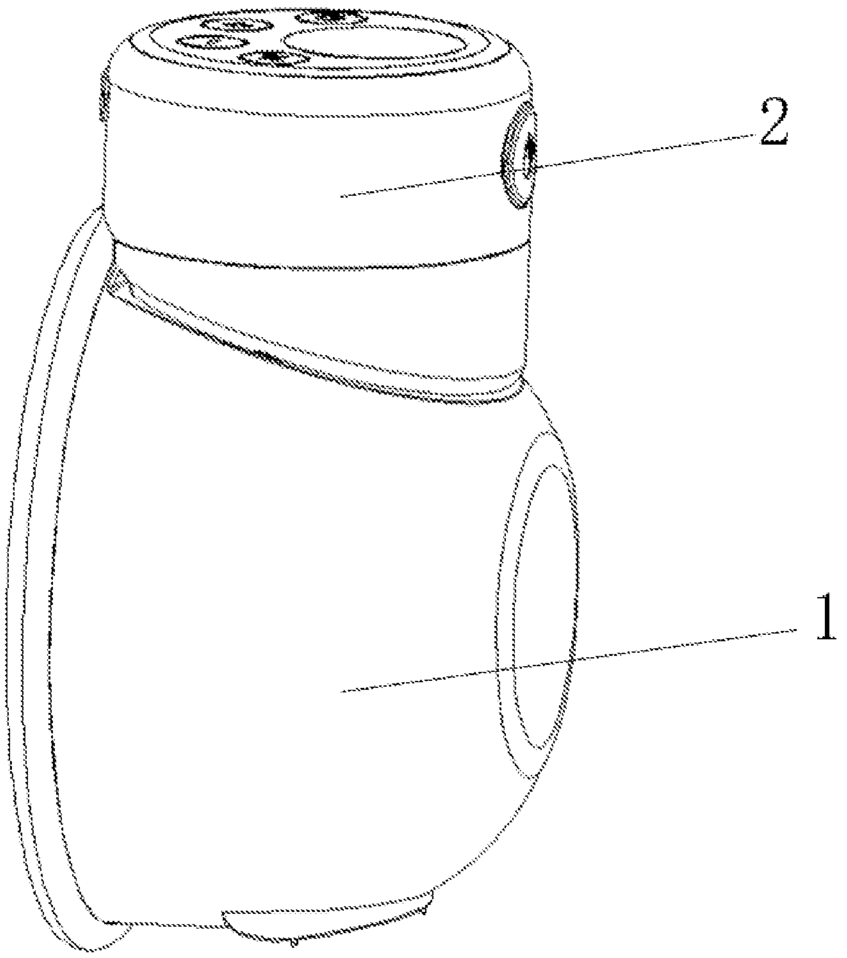
FIG. 2 is an assembly diagram of the breast pump main unit and the milk collecting casing according to the present disclosure.
Figure 3:
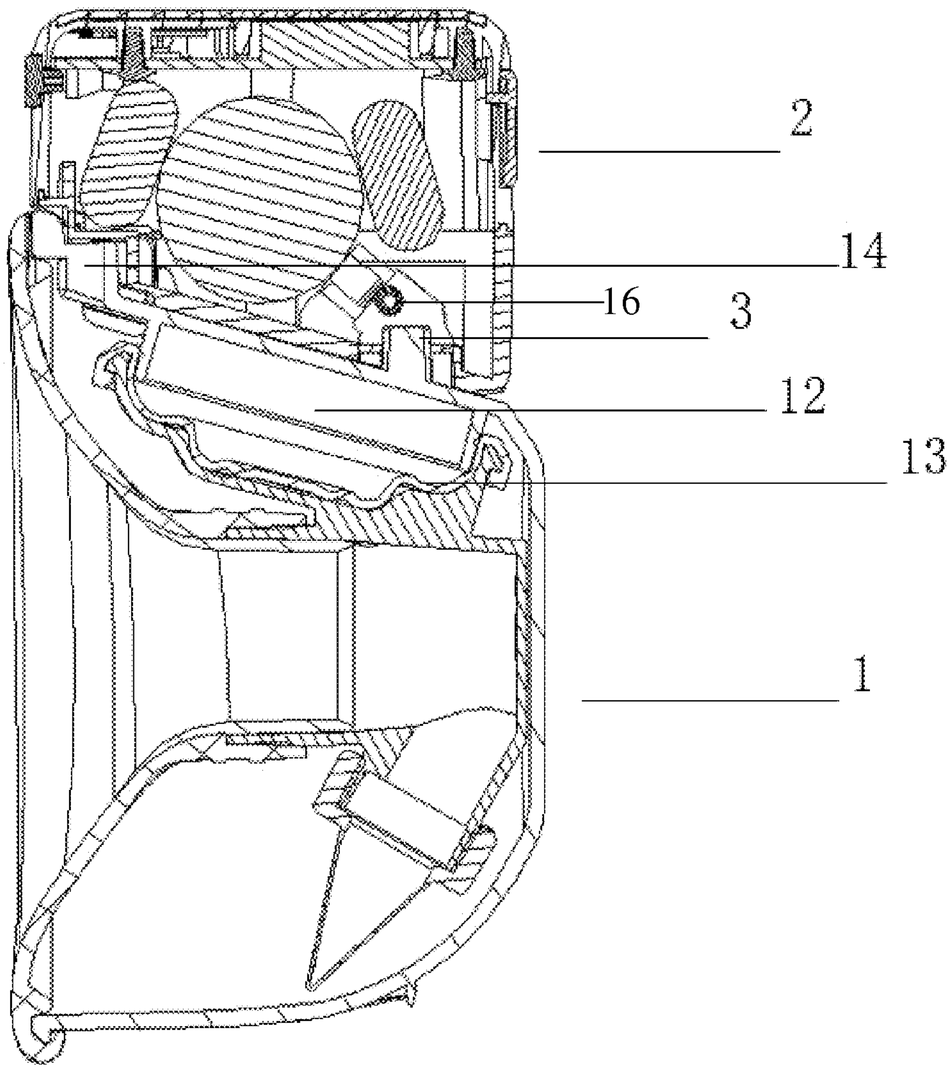
FIG. 3 is a section diagram of the breast pump according the present disclosure.

In a specific embodiment, as shown in FIGS. 1 and 3, this isolated wearable breast pump has the milk collecting casing 1 serving as a milk storage container and the breast pump main unit 2, wherein a vacuum pump and a solenoid valve are arranged inside the breast pump main unit 2, the diaphragm 13 is arranged inside the milk collecting casing 1, there is only one ventilation structure 3 connected between the milk collecting casing 1 and the breast pump main unit 2, avoiding direct contact between the breast pump main unit 2 and the diaphragm 13 inside the milk collecting casing 1 and preventing the liquid stored inside the milk collecting casing 1 from entering the breast pump main unit 2; moreover, a waterproof device is arranged on the ventilation structure 3 to further prevent the liquid inside the milk collecting casing 1 from contacting the breast pump main unit 2. Since there are many electronic elements in the breast pump main unit 2, the penetration of liquid is easy to cause a short circuit and thus damage the breast pump main unit 2, the isolated wearable breast pump provided by in the present disclosure avoids the problem that the liquid enters and damages the breast pump main unit 2.

Further, the ventilation structure 3 includes the ventilation column 32 disposed on the connection surface 4 of the milk collecting casing 1 and the breast pump main unit 2, and the ventilation hole 31 disposed on the breast pump main unit 2 and cooperating with the ventilation column 32.

Figure 4:
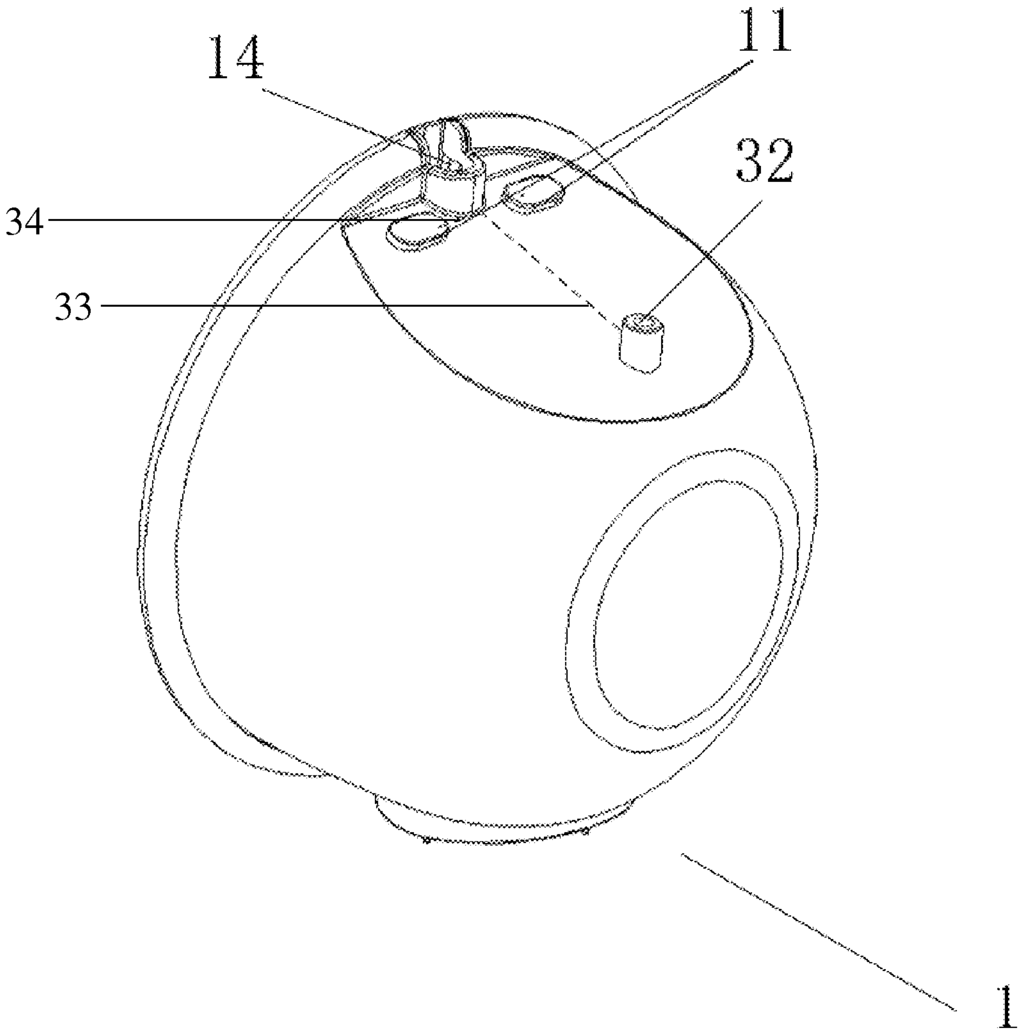
FIG. 4 is a structure view of the milk collecting casing according to the present disclosure.
Figure 5:
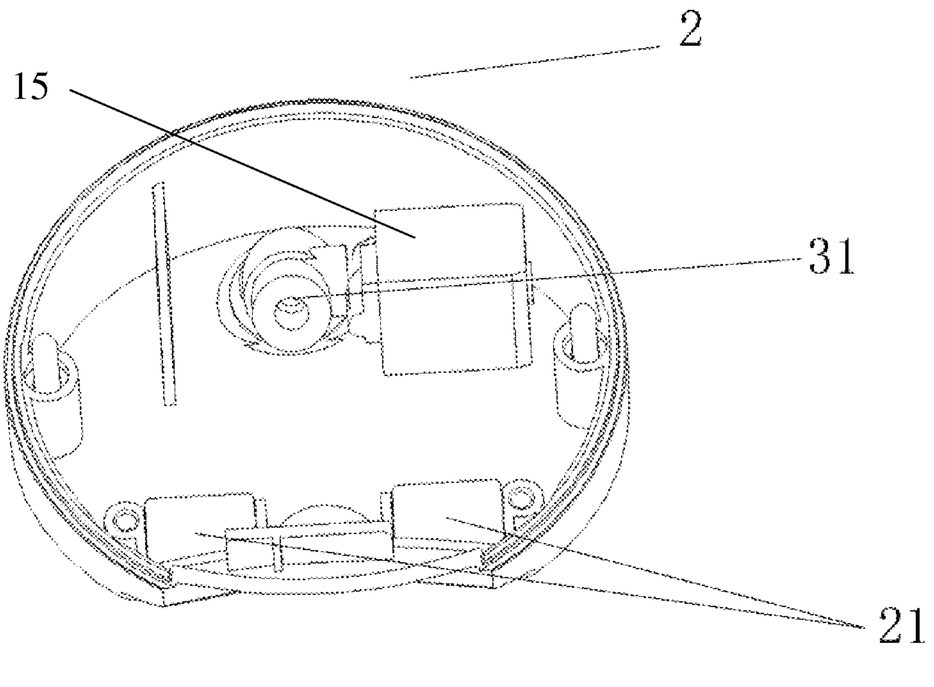
FIG. 5 is a structure view of the breast pump main unit according to the present disclosure.

In this example, as shown in the orientation of FIGS. 4 and 5, the ventilation structure 3 consists of two parts, one part is a ventilation column 32 disposed on the connection surface 4 of the top of the milk collecting casing 1 and the breast pump main unit 2, the ventilation column 32 is designed to be cylinder-shaped, and a protrusion is set on the top of the milk collecting casing 1; the other part is the ventilation hole 31 disposed on the connection surface 4 of the bottom of the breast pump main unit 2 and the milk collecting casing 1, the ventilation hole 31 sinks on the breast pump main unit 2, and the positions of the ventilation column 32 and the ventilation hole 31 fit with each other. During an actual operation, after the breast pump main unit 2 is assembled with the milk collecting casing 1, the ventilation column 32 is plugged in the ventilation hole 31, and the ventilation hole 31 just accommodates the ventilation column 32.

Here, it should be noted that there no limit to the installation position of the ventilation hole 31 and the ventilation column 32, the ventilation column 32 may be disposed on the milk collecting casing 1 as described in the above embodiment, or on the breast pump main unit 2, in the same way, the ventilation hole 31 may also be disposed on the breast pump main unit 2 or the milk collecting casing 1, as long as it is ensured that the ventilation hole 31 just accommodates the ventilation column 32 after the breast pump main unit 2 are assembled with the milk collecting casing 1. At the same time, the shape of the ventilation column 32 may be cylinder-shaped as described in the above embodiment, or it may be L-shaped, as long as it can be closely connected with the ventilation hole 31.

Further, the ventilation hole 31 adopts a soft rubber material, the ventilation column 32 adopts a hard rubber material, and the ventilation column 32 is closely plugged in and in sealing connection with the ventilation hole 31.

As shown in FIGS. 1, 4 and 5, the ventilation column 32 disposed on the milk collecting casing 1 partially adopts a hard rubber material, and the ventilation hole 31 disposed on the breast pump main unit 2 partially adopts a soft rubber material. Such design enables the ventilation column 32 to be closely plugged in and in sealing connection with the ventilation hole 31, and the assembly of the breast pump main unit 2 and the milk collecting casing 1 to be firmer without affecting its air tightness.

Further, the waterproof device comprises a waterproof membrane disposed on the ventilation column 32 and/or the ventilation hole 31.

In one specific embodiment, the waterproof device comprises a waterproof membrane disposed on the ventilation hole 31 or the ventilation column 32, the waterproof membrane is disposed at the junction of the ventilation hole 31 and the ventilation column 32, that is, it may be added to the ventilation column 32 of the milk collecting casing 1, or may be added to the ventilation hole 31 on the breast pump main unit 2, or to the both. Liquid cannot pass through the waterproof membrane, but air can pass through the waterproof membrane. The waterproof membrane here may be a waterproof membrane provided by CN208814944U, which just can function in occluding liquid and allowing gas to pass through. The waterproof membrane is configured to further prevent the milk inside the milk collecting casing 1 from entering the breast pump main unit 2 and causing short circuit damage when the diaphragm 13 is broken, and also prevent the milk from contacting the housing of the breast pump main unit 2 and causing milk to be contaminated.

A vacuum pump connected to the ventilation structure 3 and used to draw the air in the milk collecting casing 1 is arranged inside the breast pump main unit 2.

The waterproof device further includes a liquid sensor 15 disposed at the ventilation structure 3 and a waterproof valve 16 connected to the liquid sensor 15, the vacuum pump and the ventilation structure 3 intercommunicate with each other though the waterproof valve 16, which closes when the liquid sensor 15 is triggered.

Figure 6:
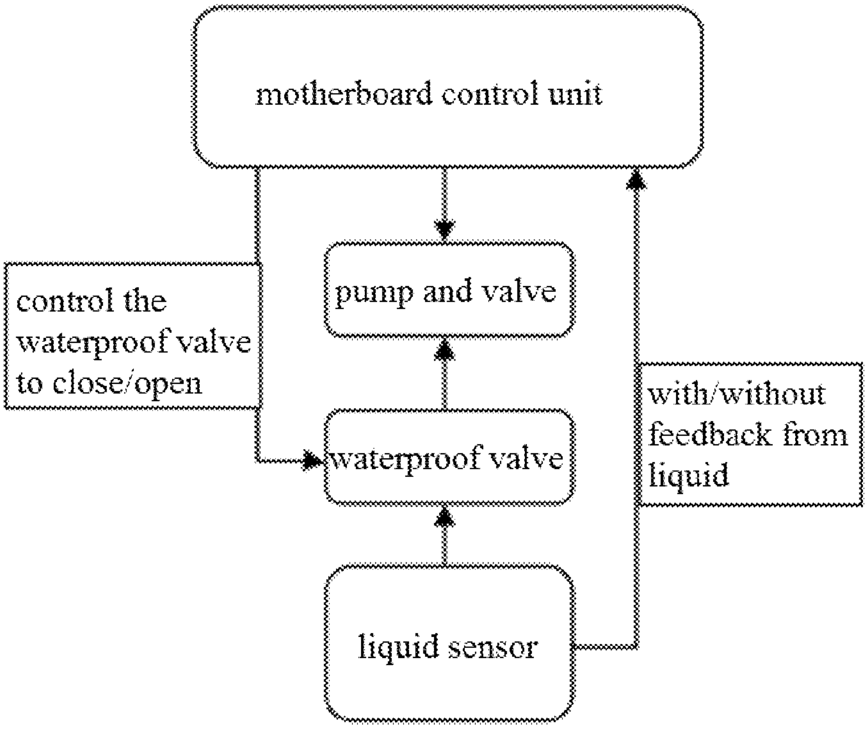
FIG. 6 is a flowchart of the waterproof device according to the present disclosure.

In one specific embodiment, as shown in FIG. 6, a vacuum pump connected to the ventilation hole 31 is arranged inside the breast pump main unit 2, and it can pump the air in the milk collecting casing 1, so as to achieve the function of sucking milk. The waterproof device further includes a liquid sensor 15, a waterproof valve 16 and a motherboard control unit, the liquid sensor 15 is provided at the soft rubber ventilation hole 31 inside the breast pump main unit, the waterproof valve 16 is further disposed close to the liquid sensor 15, and the waterproof valve 16 is connected to the soft rubber ventilation hole 31 and the vacuum pump and solenoid valve inside the breast pump main unit 2. During normal operation, the waterproof valve 16 is in an open state, so that the vacuum pump and solenoid valve draws the air inside the milk collecting casing 1 through the ventilation hole 31 and the ventilation column 32. When the liquid sensor 15 detects that liquid has entered the ventilation hole 31, the motherboard control unit will control the waterproof valve 16 to close, so as to stop the liquid from entering the breast pump main unit 2. When the liquid sensor 15 does not sense the liquid in the ventilation hole 31, the motherboard control unit then controls the waterproof valve 16 to open. This further prevents milk from entering the breast pump main unit 2 and causing short-circuit damage and avoids contamination of milk in contact with the surroundings.

At least one first suction member 11 is disposed on the connection surface 4 between the milk collecting casing 1 and the breast pump main unit 2, and at least one second suction member 21 is disposed at the position fitting 22 with the breast pump main unit 2.

In one embodiment, there are two first suction members 11, and the ventilation structure 3 is arranged on the perpendicular bisector 33 of the connection line 34 of the two first suction members 11, so that the breast pump main unit 2 is more firmly connected with the milk collecting casing 1.

The attraction between the first suction member 11 and the second suction member 21 may be that between two magnets, or a magnet and a metal, or other two materials or elements with attraction capacity. In one specific embodiment, the first suction member 11 and the second suction member 21 are magnets, as shown in the orientation shown in FIG. 1, two first suction members 11 are disposed at the top of the milk collecting casing 1, two second suction members 21 are disposed at the bottom of the breast pump main unit 2, the first suction members 11 and the second suction members 21 are arranged at the same position after the breast pump main unit 2 is assembled with the milk collecting casing 1, thus the breast pump main unit 2 is connected and fixed to the milk collecting casing 1 by device of magnetization, so that the assembly is firmer. The ventilation structure 3, the first suction member 11 and the second suction member 21 are positioned on both sides of the central axis of the wearable breast pump, respectively, close to the connection surface 4 of the central the breast pump main unit 2 and the milk collecting casing 1, the ventilation hole 31 and the second suction member 21 are disposed at the bottom of the breast pump main unit 2, and the ventilation column 32 and the first suction member 11 are disposed on the top of the milk collecting casing 1, so that the insertion of the ventilation column 32 and the ventilation port 31 cooperates with the magnetic connection of the first suction member 11 and the second suction member 21, so as to enable the breast pump main unit 2 to be connected and fixed to the milk collecting casing 1.

The milk collecting casing 1 further has a connecting portion for fitting with mammillae, and a negative pressure cavity 12 connected to the connecting portion.

The breast pump main unit 2 is connected to the negative pressure cavity 12 and used to draw air in the negative pressure cavity 12.

In one specific embodiment, as shown in the orientation shown in FIG. 3, the milk collecting casing 1 has a connecting portion wearable on the breast, and a negative pressure cavity 12 positioned above the connecting portion, the diaphragm 13 is arranged inside the negative pressure cavity 12, and the negative pressure cavity 12 is connected to the breast pump main unit 2 by device of the ventilation column 32, so that the vacuum pump inside the breast pump main unit 2 drives the diaphragm 13 to move forwards and backwards by drawing the air in the negative pressure cavity 12 so as to achieve the function of sucking milk.

Further, the connection surface 4 between the milk collecting casing 1 and the breast pump main unit 2 is provided with the milk pouring port 14, which has an inclination towards the outside of the milk collecting casing 1.

In one specific embodiment, as shown in the orientation of FIGS. 3 and 4, the top of the milk collecting casing 1 is further provided with the milk pouring port 14, which is connected to the area storing milk inside the milk collecting casing 1, and the milk stored in the milk collecting casing 1 is poured out for use through the milk pouring port 14. Since the milk pouring port 14 has a certain inclination, the milk pouring port 14 forms an arc, which can prevent the milk from being scattered when the milk is poured out.

Compared with the prior art, in the existing breast pump, the surface of the main unit is in direct contact with the diaphragm 13 of the milk storage container to form a negative pressure cavity, which enables the diaphragm 13 to move forwards and backwards under the cooperation of the vacuum pump and the solenoid valve, so as to achieve sucking milk. Such breast pump main unit is sealed with the diaphragm 13 of the breast storage container by generally squeezing soft rubber in a large range, but since the diaphragm 13 must be disassembled before and after use to clean and disinfect, such high frequency for use results in the diaphragm 13 being an easily-damaged consumable. After the diaphragm 13 is broken, the milk in the milk storage container is easy to contact the main unit at the part where the breast pump main unit 2 is directly connected with the diaphragm 13, on the one hand, resulting in the milk being contaminated, on the other hand easily leading to damage to the main unit.

Since the isolated wearable breast pump provided by the present disclosure only has one ventilation structure 3 connecting the breast pump main unit 2 with the milk collecting casing 1, it can completely eliminate the contact between the internal diaphragm 13 inside the milk collecting casing 1 and the breast pump main unit 2, even if the diaphragm 13 is broken, it can reduce the contact between milk and the breast pump main unit 2. The present disclosure also provides a waterproof device on the ventilation structure 3, on the one hand, to reduce the risk of contamination arising from milk's contact with the breast pump main unit 2, and on the other hand, to avoid the breast pump main unit 2 from damaging due to milk's penetration.

The aforementioned examples are only a better embodiment of the present disclosure and are not intended to limit the present disclosure, and any modification, equivalent replacement and improvement made within the essence and principle of the present disclosure shall be included in the protection scope of the present disclosure.

What is claimed is:

1. An isolated wearable breast pump comprising a milk collecting casing for storing milk, and a breast pump main unit connected to said milk collecting casing for drawing air inside said milk collecting casing, wherein a connection surface between said milk collecting casing and said breast pump main unit is provided with a ventilation structure, which is provided with a waterproof device used to prevent liquid from entering said breast pump main unit;

wherein said ventilation structure includes a ventilation column disposed on the connection surface of said milk collecting casing and said breast pump main unit, and a ventilation hole disposed on said breast pump main unit and cooperating with said ventilation column; wherein said waterproof device further includes a liquid sensor disposed at said ventilation structure, a waterproof valve connected to said liquid sensor, and a motherboard control unit; when the liquid sensor detects that liquid has entered the ventilation hole, the motherboard control unit is configured to automatically control the waterproof valve to close, so as to stop the liquid from entering the breast pump main unit; and when the liquid sensor does not sense the liquid in the ventilation hole, the motherboard control unit then is configured to automatically control the waterproof valve to open;

wherein the liquid sensor is provided at the ventilation hole inside the breast pump main unit; and wherein two first suction members are disposed on the connection surface, and the ventilation structure is positioned on a perpendicular bisector of a connection line between the two first suction members.

2. The isolated wearable breast pump according to claim 1, wherein said ventilation hole adopts a soft rubber material, said ventilation column adopts a hard rubber material, and said ventilation column is closely plugged in and in sealing connection with said ventilation hole.

3. The isolated wearable breast pump according to claim 2, wherein said waterproof means-device comprises a waterproof membrane disposed on said ventilation hole and/or said ventilation column.

4. The isolated wearable breast pump according to claim 1, wherein at least one first suction member is disposed on the connection surface between said milk collecting casing and said breast pump main unit, and at least one second suction member is disposed at a position fitting with said breast pump main unit.

5. The isolated wearable breast pump according to claim 4, wherein said two first suction members, and said ventilation structure is arranged on a perpendicular bisector of a connection line of said two first suction members, so that said breast pump main unit is more firmly connected with said milk collecting casing.

6. The isolated wearable breast pump according to claim 1, wherein said milk collecting casing further has a connecting portion for fitting with mammillae, and a negative pressure cavity disposed inside the connection surface and communicating with said breast pump main unit.

7. The isolated wearable breast pump according to claim 1, wherein the connection surface between said milk collecting casing and said breast pump main unit is provided with a milk pouring port, which has an inclination towards an outside of said milk collecting casing.

* * * * *